(12) United States Patent
Jones et al.

(10) Patent No.: US 9,394,317 B2
(45) Date of Patent: Jul. 19, 2016

(54) IMIDAZO PYRIDINE COMPOUNDS

(71) Applicant: Eli Lilly and Company, Indianapolis, IN (US)

(72) Inventors: Spencer Brian Jones, Fishers, IN (US); Bryan Hurst Norman, Indianapolis, IN (US); Lance Allen Pfeifer, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/761,008

(22) PCT Filed: Mar. 4, 2014

(86) PCT No.: PCT/US2014/020297
§ 371 (c)(1),
(2) Date: Jul. 15, 2015

(87) PCT Pub. No.: WO2014/143583
PCT Pub. Date: Sep. 18, 2014

(65) Prior Publication Data
US 2015/0368273 A1    Dec. 24, 2015

Related U.S. Application Data

(60) Provisional application No. 61/777,216, filed on Mar. 12, 2013.

(51) Int. Cl.
| | | |
|---|---|---|
| *A61K 31/519* | (2006.01) |
| *C07D 519/00* | (2006.01) |
| *C07D 471/02* | (2006.01) |
| *C07D 487/02* | (2006.01) |
| *C07D 491/02* | (2006.01) |

(52) U.S. Cl.
CPC ............ *C07D 519/00* (2013.01); *C07D 471/02* (2013.01); *C07D 487/02* (2013.01); *C07D 491/02* (2013.01)

(58) Field of Classification Search
CPC ...................................................... C07D 519/00
See application file for complete search history.

(56) References Cited

U.S. PATENT DOCUMENTS

| 7,524,852 B2 | 4/2009 | Arai et al. |
| 2007/0249631 A1 | 10/2007 | Oberboersch |

FOREIGN PATENT DOCUMENTS

| WO | 01/32632 | 5/2001 |
| WO | 2011/048477 | 4/2011 |

*Primary Examiner* — Brian McDowell
(74) *Attorney, Agent, or Firm* — Macharri R. Vorndran-Jones

(57) ABSTRACT

The present invention provides compounds of the formula I, wherein X is a bond or $CH_2$; Q is $CH_2$ or O; L is selected from the group consisting of —$OCH_2$— and —$CH_2O$—; or a pharmaceutically acceptable salt thereof. Compounds of the invention are autotaxin inhibitors.

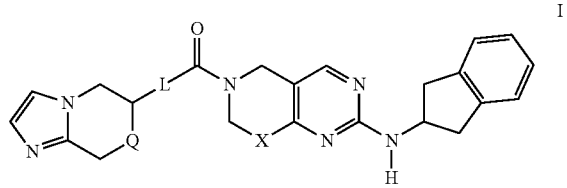

9 Claims, No Drawings

IMIDAZO PYRIDINE COMPOUNDS

This invention relates to imidazo pyridine and imidazo morpholine compounds, or pharmaceutically acceptable salts thereof, and therapeutic use thereof. Compounds of this invention are autotaxin inhibitors.

Autotaxin is an enzyme reported to be the source of lysophosphatidic acid (LPA) which up-regulates pain-related proteins through one if its cognate receptors, $LPA_1$. LPA is an intracellular lipid mediator which influences a multiplicity of biological and biochemical processes. Targeted inhibition of autotaxin-mediated LPA biosynthesis may provide a novel mechanism to prevent nerve injury-induced neuropathic pain. Compounds that inhibit autotaxin are desired to offer a potential treatment option for patients in need of treatment for pain.

Pain associated with osteoarthritis (OA) is reported to be the primary symptom leading to lower extremity disability in OA patients. Over 20 million Americans have been diagnosed with OA, the most common of the arthropathies. The currently approved treatments for OA pain may be invasive, lose efficacy with long term use, and may not be appropriate for treating all patients. Additional treatment options for patients suffering from pain associated with OA are desired. Compounds that inhibit autotaxin represent another possible treatment option for patients with pain associated with OA.

U.S. Pat. No. 7,524,852 ('852) discloses substituted bicyclic pyrimidine derivatives as anti-inflammatory agents.

PCT/US2011/048477 discloses indole compounds as autotoxin inhibitors.

There is a need for novel autotaxin inhibitors. The present invention provides novel compounds which are autotaxin inhibitors. The present invention provides certain novel compounds that inhibit the production of LPA. Autotaxin inhibitor compounds are desired to provide treatments for autotaxin mediated conditions, such as pain associated with OA.

The present invention provides compounds of Formula I

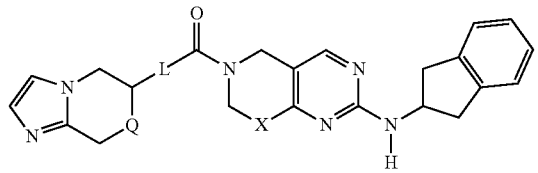

wherein X is a bond or $CH_2$;
Q is $CH_2$ or O;
L is selected from the group consisting of —$OCH_2$— and —$CH_2O$—;
or a pharmaceutically acceptable salt thereof.

The present invention also provides a method of treating pain in a patient, comprising administering to a patient in need of such treatment an effective amount of a compound of Formula I, or a pharmaceutically acceptable salt thereof. The present invention also provides a method of treating pain associated with osteoarthritis in a patient, comprising administering to a patient in need of such treatment, an effective amount of a compound of Formula I, or a pharmaceutically acceptable salt thereof.

This invention provides a compound of Formula I, or a pharmaceutically acceptable salt thereof, for use in therapy, in particular for the treatment of pain or for the treatment of pain associated with OA. Even furthermore, this invention provides the use of a compound of Formula I, or a pharmaceutically acceptable salt thereof, for the manufacture of a medicament for the treatment of pain. This invention also provides the use of a compound of Formula I, or a pharmaceutically acceptable salt thereof, for the manufacture of a medicament for the treatment of pain associated with OA.

The invention further provides a pharmaceutical composition, comprising a compound of Formula I, or a pharmaceutically acceptable salt thereof, in combination with one or more pharmaceutically acceptable carriers, diluents, or excipients. The invention also encompasses novel intermediates and processes for the synthesis of the compounds of Formula I.

The term "pharmaceutically-acceptable salt" refers a salt of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "treating" (or "treat" or "treatment") as used herein refers to restraining, slowing, stopping, or reversing the progression or severity of an existing symptom, condition, or disorder. Symptoms, conditions, or disorders may present as "acute" or "chronic" events. In an acute event compound is administered at the onset of symptom, condition, or disorder and discontinued when the event disappears. A chronic event is treated during the course of the disorder or condition associated with the symptom or event, wherein the chronic treatment is not dependent on a particular manifestation of the symptom or event. The present invention contemplates both acute and chronic treatment.

Compounds of the present invention inhibit autotaxin, and may be useful for treating a disease or condition accompanied by an increase in autotaxin. Compounds of the present invention inhibit the production of LPA and may be useful for treating a disease or condition accompanied by an increase in LPA. Compounds of this invention may inhibit autotaxin mediated LPA biosynthesis when compared to other LPA lipid mediators. Compounds of this invention may be useful for treating a disease or condition accompanied by an increase in LPA.

As used herein, "patient" refers to an animal in need of treatment, preferably not exclusively a mammal. A preferable embodiment is a patient that is a mammal, which is preferably a human. Another preferable embodiment is a patient that is a companion animal such as a dog, cat; or a fowl.

As used herein, the term "effective amount" refers to the amount or dose of compound of the invention or a pharmaceutically acceptable salt thereof which upon single or multiple dose administration to the patient, provides the desired effect in the patient under diagnosis or treatment. It will be understood that the amount of active agent actually administered will be determined by a physician, in light of the relevant circumstances, including the condition to be treated, the chosen route of administration, the actual active agent administered, the age, weight, and response of the individual patient, and the severity of the patient's symptoms and other relevant circumstances.

A compound of the present invention is preferably formulated as pharmaceutical compositions administered by any route which makes the compound bioavailable. Most preferably, such compositions are for oral administration. Such pharmaceutical compositions and processes for preparing same are well known in the art. See, e.g., *Remington: The Science and Practice of Pharmacy* (D. B. Troy, Editor, 21st Edition, Lippincott, Williams & Wilkins, 2006).

The compounds of Formula I are particularly useful in the treatment methods of the invention, but certain groups, substituents, and configurations are preferred for compounds of Formula I. The following paragraphs describe such preferred groups, substituents, and configurations. It will be understood that these preferences are applicable both to the treatment methods and to the new compounds of the invention.

It is preferred that X is selected from the group consisting of a bond or $CH_2$. It is especially preferred that X is a bond.

It is preferred that L is —$CH_2O$—.

It is especially preferred that when X is a bond, Q is O, and L is —$CH_2O$—.

It is further preferred that X is a bond, Q is $CH_2$, and L is —$CH_2O$—.

Preferred compounds are:
5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate;
5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate;
1-[2-(2,3-dihydro-1H-inden-2-ylamino)-5,7-dihydro-6H-pyrrolo[3,4-d]pyrimidin-6-yl]-2-(5,6,7,8-tetrahydroimidazo[1,2-a]pyridin-6-yloxy)ethanone;
1-[2-(2,3-dihydro-1H-inden-2-ylamino)-7,8-dihydropyrido[4,3-d]pyrimidin-6(5H)-yl]-2-(5,6,7,8-tetrahydroimidazo[1,2-a]pyridin-6-yloxy)ethanone, and
the pharmaceutically acceptable salts thereof.

Preferred compounds are:
5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate;
5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate, and
the pharmaceutically acceptable salts thereof.

Especially preferred compounds are:
[(6R)-6,8-dihydro-5H-imidazo[2,1-c][1,4]oxazin-6-yl]methyl 2-(indan-2-ylamino)-5,7-dihydropyrrolo[3,4-d]pyrimidine-6-carboxylate, and
the pharmaceutically acceptable salts thereof.

Especially preferred compounds are:
5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate, and
the pharmaceutically acceptable salts thereof.

PREPARATIONS AND EXAMPLES

The following Preparations and Examples further illustrate the invention and represent a typical synthesis of the compound of the invention. It should be understood that the Preparations and Examples are set forth by way of illustration and not limitation, and that various modifications may be made by one of ordinary skill in the art. In the schemes presented below, all substituents, unless otherwise indicated, are as previously defined. Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated or resolved by one of ordinary skill in the art at any convenient point in the synthesis of compounds of Formula I by methods such as selective crystallization techniques or chiral chromatography (see for example, J. Jacques, et al., "*Enantiomers, Racemates, and Resolutions*", John Wiley and Sons, Inc., 1981, and E. L. Eliel and S. H. Wilen "*Stereochemistry of Organic Compounds*", Wiley-Interscience, 1994). The reagents and starting materials are generally available to one of ordinary skill in the art. Others may be prepared by standard techniques of organic and heterocyclic chemistry which are analogous to the synthesis of known structurally similar compounds and procedures described by the Preparations and Examples which follow, including any novel procedures.

Unless noted to the contrary, the compounds illustrated herein are named and numbered using either ACDLABS or Symyx Draw 3.2.

Generally, a compound of formula I where X is a bond or $CH_2$ may be prepared from a compound of formula II. More specifically in Scheme A, a compound of formula II where X is a bond or $CH_2$ is coupled with a compound of formula VII where Q is $CH_2$ or O in the presence of carbonyldiimidazole (CDI) and a base such as triethylamine to provide a compound of formula Ia where X is a bond or $CH_2$, and Q is $CH_2$ or O. The reaction is conveniently carried out in a solvent such as dichloromethane.

Alternatively in Scheme A, a compound of formula I where X is a bond or $CH_2$ and Q is $CH_2$ may be prepared from a compound of formula III. More specifically, a compound of formula III where Q is $CH_2$ is reacted with an acid such as trifluoroacetic acid in a solvent such as dichloromethane to provide the corresponding carboxylic acidI. The intermediate carboxylic acid is reacted with a compound of formula II where X is a bond or $CH_2$ and 1-propanephosphonic acid cyclic anhydride in the presence of a base such as triethylamine to provide a compound of formula Ib where X is a bond or $CH_2$, and Q is $CH_2$. The reaction is conveniently carried out in a solvent such as dimethylformamide.

A compound of formula VII where Q is $CH_2$ or O or a compound of formula III where Q is $CH_2$ may be prepared as described in the preparations or by procedures known to one of ordinary skill in the chemical art.

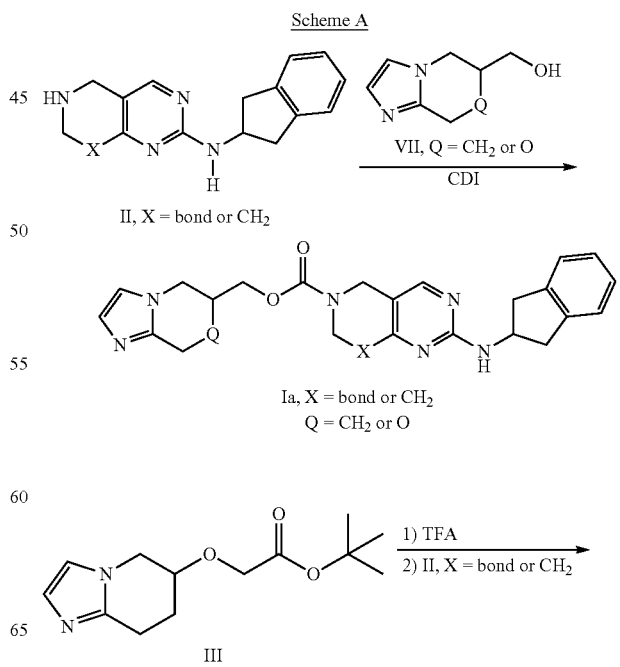

Scheme A

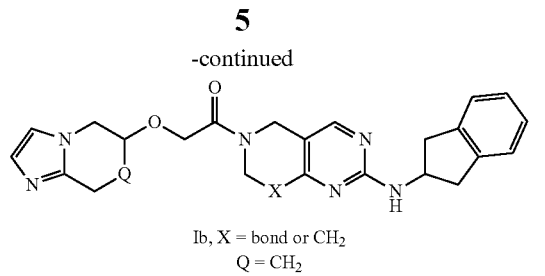

Ib, X = bond or CH₂
Q = CH₂

As shown in Scheme B, a compound of formula II where X is a bond or CH₂ may be prepared from a compound of formula V where Pg is an amine protecting group. More specifically, a compound of formula V where X is a bond or CH₂, and Pg is tert-butoxycarbonyl is reacted with an acid such as hydrochloric acid in a solvent such as tetrahydrofuran to provide a compound of formula II where X is a bond or CH₂.

Scheme B

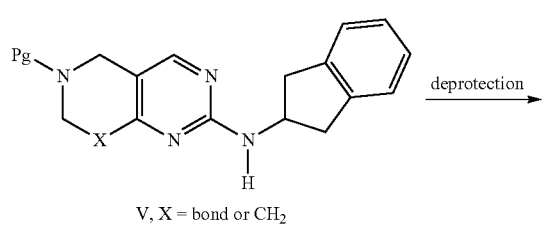

V, X = bond or CH₂

↓ deprotection

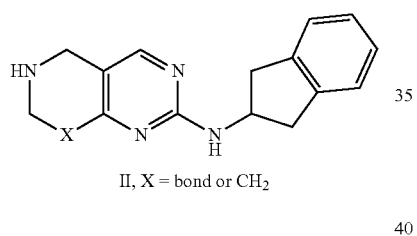

II, X = bond or CH₂

In Scheme C, a compound of formula V where X is CH₂; and Pg is an amine protection group such as tert-butoxycarbonyl may be prepared from a compound of formula VI. More specifically, a protected-4-piperidone is reacted sequentially with (CH₃)₂NCH(OCH₃)₂ in a solvent such as dimethylformamide, and then with a compound of formula VI, a base such as potassium carbonate in a co-solvent such as ethanol to provide a compound of formula V where X is CH₂, and Pg is tert-butoxycarbonyl. A compound of formula VI may be prepared by reacting 2,3-dihydro-1H-inden-2-amine hydrochloride with 1H-pyrazole-1-carboximidamide hydrochloride and a base such as diisopropylethylamine in a solvent such as acetonitrile.

Scheme C

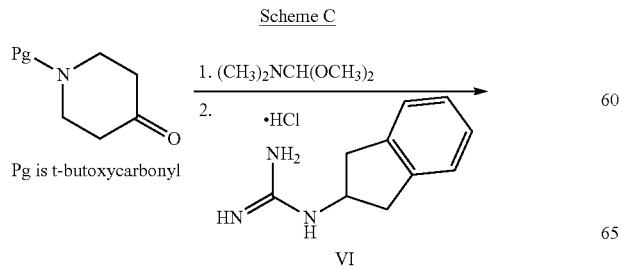

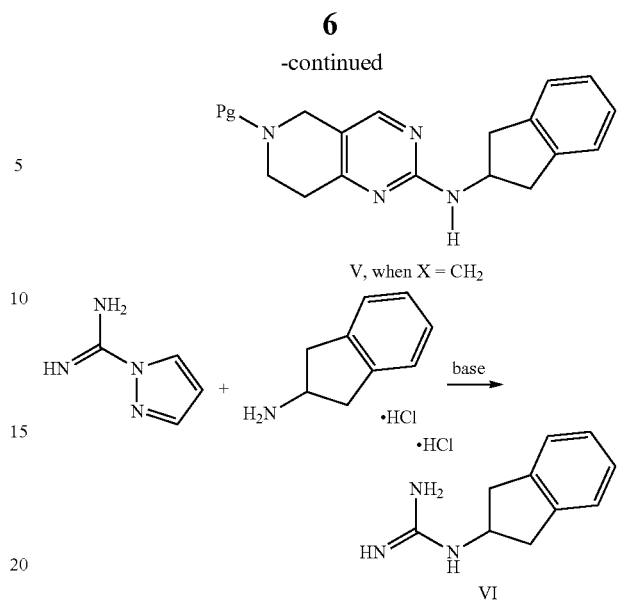

V, when X = CH₂

+ (pyrazole carboximidamide) + (indanamine·HCl) —base→ VI

In Scheme D, a compound of formula V where X is a bond and Pg is an amine protecting group such as tert-butoxycarbonyl may be prepared by reacting tert-butyl 2-chloro-5,7-dihydro-6H-pyrrolo[3,4-d]pyrimidine-6-carboxylate with 2,3-dihydro-1H-inden-2-amine in the presence of a base such as N-ethyl-N-isopropylpropan-2-amine in a solvent as 1-methylpyrrolidin-2-one.

Scheme D

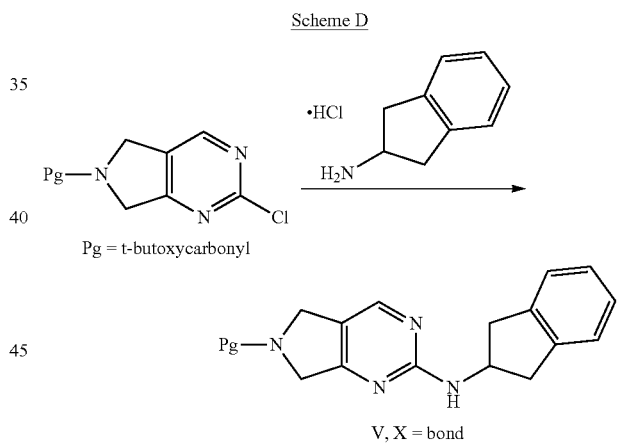

Pg = t-butoxycarbonyl

V, X = bond

Preparation 1

Synthesis of
1-(2,3-dihydro-1H-inden-2-yl)guanidine
hydrochloride

Stir a solution of 2,3-dihydro-1H-inden-2-amine hydrochloride (197 g; 1.08 equiv; 1.16 moles), 1H-pyrazole-1-carboximidamide hydrochloride (158 g; 1.00 equiv; 1.08 moles) and diisopropylethylamine (400 g; 2.87 equiv; 3.09 moles; 539.74 mL) in acetonitrile (2 L) at 62° C. for 2 hours, during which time a white solid precipitates. Cool the mixture to 25° C., then filter and wash with 300 mL acetonitrile and 300 mL methyltert-butyl ether. Dry the product in air at 25° C. for 1 h to afford the title compound (200 g, 87%) as a white solid. MS (m/z): 176 (M+1).

Preparation 2

Synthesis of tert-butyl 2-(indan-2-ylamino)-7,8-dihydro-5H-pyrido[14,3-d]pyrimidine-6-carboxylate

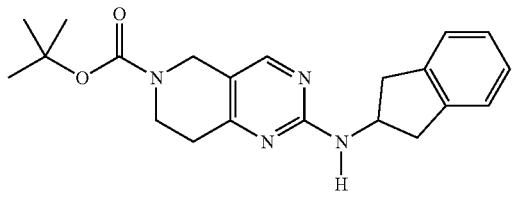 [SMILES: CC(C)(C)OC(=O)N1CCc2nc(NC3Cc4ccccc4C3)ncc2C1]

Stir a solution of 1,1-dimethoxy-N,N-dimethyl-methanamine (224 g; 2.15 equiv; 1.88 moles; 250.98 mL) and N-t-butoxycarbonyl-4-piperidone (250 g; 1.44 equiv; 1.25 moles) in dimethylformamide (1.2 L) at 109° C. under $N_2$ for 4 h. Cool the mixture to 25° C. and then add ethanol (700 mL; 12.02 moles; 553.91 g). Add 1-(2,3-dihydro-1H-inden-2-yl) guanidine hydrochloride (185 g; 1.00 equiv; 873.90 mmoles) and potassium carbonate (475 g; 3.44 moles) to the mixture at 25° C. in one portion to form a white suspension. Stir the mixture at 80-90° C. for 24 h, then cool to 25° C. and pour the mixture into 5 L ice/water to get a yellow suspension. Extract with ethyl acetate (3×3 L), and wash the organic layer with 10% lithium chloride solution (3 L), water (3 L), and saturated sodium chloride solution (3 L). Dry over anhydrous sodium sulfate, filter and concentrate to give about 300 ml of a red solution. Filter the solution through a silica gel plug (10 cm height, 5 cm diameter) and then concentrate to dryness to give the title compound as a red gel (320 g, 100%). MS (m/z): 367 (M+1).

Preparation 3

Synthesis of N-indan-2-yl-5,6,7,8-tetrahydropyrido[4,3-d]pyrimidin-2-amine

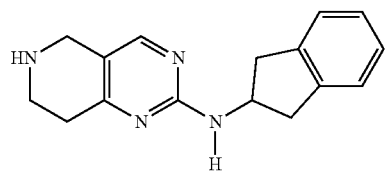 [SMILES: c1ccc2c(c1)CC(Nc1ncc3c(n1)CCNC3)C2]

Add portionwise hydrochloric acid (900 mL; 5M in water; 5.17 equiv; 4.50 mole; 1.08 kg) to a solution of tert-butyl 2-(indan-2-ylamino)-7,8-dihydro-5H-pyrido[4,3-d]pyrimidine-6-carboxylate (319 g; 1.00 equiv; 870.48 mmoles) in tetrahydrofuran (1.5 L). Once the addition is complete, stir the solution at 50° C. for 1 h. Cool the mixture to 25° C. and then add 3 L methyltert-butyl ether and 1 L water. Allow the solution to stand at 20° C. for 16 h. Separate the phases and extract the aqueous phase with dichloromethane (2 L). Discard the organic extracts and adjust the aqueous phase to pH 10 using 4M sodium hydroxide. Extract with ethyl acetate (3×3 L), and wash the combined organic extracts with saturated sodium chloride (2 L). Dry over anhydrous sodium sulfate, filter and concentrate to dryness to give a red gel. Redissolve the substance in ethyl acetate (300 mL) and petroleum ether (200 mL) at 50° C., and allow for precipitation over 24 hours. Filter and dry to afford the title compound (85 g, 37%). MS (m/z): 267 (M+1).

Preparation 4

Synthesis of tert-butyl-2-(2,3-dihydro-1H-inden-2-ylamino)-5,7-dihydro-6H-pyrrolo[3,4-d]pyrimidine-6-carboxylate

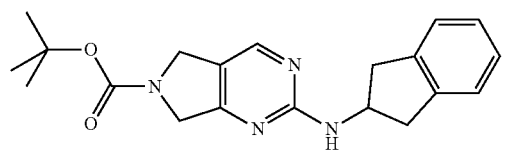 [SMILES: CC(C)(C)OC(=O)N1Cc2cnc(NC3Cc4ccccc4C3)nc2C1]

Charge 450 mL (2.58 mol) of N-ethyl-N-isopropylpropan-2-amine into a 15° C. solution of tert-butyl 2-chloro-5,7-dihydro-6H-pyrrolo[3,40d]pyrimidine-6-carboxylate (220 g, 860.37 mmol) and 2,3-dihydro-1H-inden-2-amine (137.7 g, 1.03 mol) in 1-methylpyrrolidin-2-one (3.6 L). Heat the resulting mixture to 80° C. for 16 h, then cool to 30° C. and transfer the resulting mixture into 5 L of water at 25° C. Filter the resulting solid and rinse the filter cake with water (2×300 mL). Reslurry the solid in ethyl acetate (350 mL) for 45 min at 15° C. Filter the slurry, rinsing with 15° C. ethyl acetate (2×250 mL), and dry to give the title compound (226 g, 75%) as an off-white solid. $^1$H NMR ($d_6$-DMSO) 1.45 (s, 9 H), 2.87 (dd, J=7.2, 15.8 Hz, 2 H), 3.24 (dd, J=7.2, 15.8 Hz, 2 H), 4.36 (d, 10.4 Hz, 2 H), 4.44 (d, J=12.8 Hz, 2 H), 4.60 (m, 1 H), 7.14 (m, 2 H), 7.20 (m, 2 H), 7.55 (d, J=6.8 Hz, 1 H), 8.27 (d, J=7.2 Hz, 1 H).

Preparation 5

Synthesis of N-(2,3-dihydro-1H-inden-2-yl)-6,7-dihydro-5H-pyrrolo[3,4-d]pyrimidin-2-amine dihydrochloride hydrate

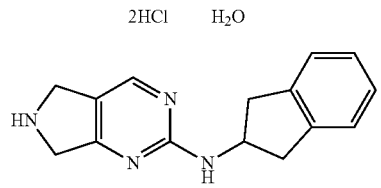 [SMILES: O ; c1ccc2c(c1)CC(Nc1ncc3c(n1)CNC3)C2]

Charge 670 mL of 5 M hydrochloric acid (3.35 mol) to a solution of tert-butyl 2-(2,3-dihydro-1H-inden-2-ylamino)-5,7-dihydro-6H pyrrolo[3,4-d]pyrimidine-6-carboxylate (226 g, 641.25 mmol) in tetrahydrofuran (2.0 L) at 17° C., maintaining the internal temperature below 26° C. during the addition. Heat the resulting solution to 50° C. for 16 h, cool to 25° C. and dilute with 500 mL of water and 500 mL of tert-butylmethylether. Separate the resulting layers and extract with tert-butylmethylether (3×1 L). Concentrate the water phase down to a reaction volume of ca. 200 mL, and filter the resulting slurry. Rinse the cake with tert-butylmethylether (2×200 mL) and dry to give the title product (177 g, 80%) as a light brown solid. MS (m/z): 253.2 (M-2HCl—H$_2$O+1).

Preparation 6

Synthesis of ethyl 5,6,7,8-tetrahydroimidazo[1,2-a]pyridine-6-carboxylate hydrochloride

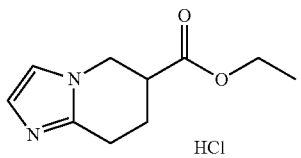

Add 5 N hydrochloric acid (100 mL; 500.00 mmoles) and ethanol (200 mL) to a flask containing methyl imidazo[1,2-a]pyridine-6-carboxylate (4.98 g; 1.0 equiv; 28.27 mmoles) and 10% palladium on carbon (3.01 g; 0.1 equiv; 2.83 mmoles). Evacuate and backfill the reaction vessel with nitrogen (3×), then re-evacuate and backfill the reaction with hydrogen (3×). Heat the reaction mixture to 60° C. and vigorously stir under a hydrogen atmosphere for 24 hours, then evacuate and backfill the reaction vessel with nitrogen (3×) and filter the reaction mixture through Celite™, rinsing the filter cake with ethanol (100 mL). Concentrate the filtrate, add toluene (200 mL), and concentrate to dryness (repeat 2 times) to afford ethyl 5,6,7,8-tetrahydroimidazo[1,2-a]pyridine-6-carboxylate hydrochloride (5.74 g; 88%) as a white solid. MS (m/z): 195(M+1).

Preparation 7

Synthesis of 5,6,7,8-tetrahydroimidazo[1,2-a]pyridin-6-ylmethanol

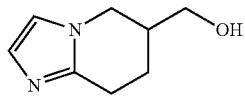 [SMILES: OCC1CCc2nccn2C1]

Suspend ethyl 5,6,7,8-tetrahydroimidazo[1,2-a]pyridine-6-carboxylate hydrochloride (5.74 g; 1.0 equiv; 24.88 mmoles) in dichloromethane (100 mL), and tetrahydrofuran (40 mL) and cool to 0° C. Add lithium aluminum hydride (1.77 g; 1.8 equiv; 44.79 mmoles) portionwise over 10 minutes. After an additional 5 minutes, allow the reaction mixture to warm to ambient temperature. After 15 minutes, cool the reaction mixture to 0° C. and slowly add water (1.77 mL), 15% sodium hydroxide solution (1.77 mL), and water (5.31 mL) sequentially with vigorous stirring. Continue to stir at ambient temperature for 15 minutes. Add magnesium sulfate then filter the reaction mixture, rinsing the filter cake with 200 mL dichloromethane. Concentrate the filtrate to give 5,6,7,8-tetrahydroimidazo[1,2-a]pyridin-6-ylmethanol (2.63 g; 69%). MS (m/z): 153(M+1).

Example 1

Synthesis of 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate

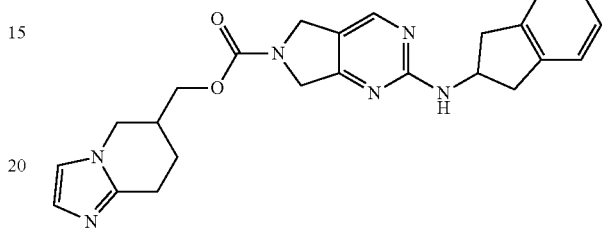

Add 1,1'-carbonyldiimidazole (2.87 g; 1.02 equiv; 17.69 mmoles) to a solution of 5,6,7,8-tetrahydroimidazo[1,2-a]pyridin-6-ylmethanol (2.64 g; 1.00 equiv; 17.35 mmoles) in dichloromethane (30 mL), then stir at 40° C. for 1 hour. Add N-(2,3-dihydro-1H-inden-2-yl)-6,7-dihydro-5H-pyrrolo[3,4-d]pyrimidin-2-amine dihydrochloride hydrate (6.25 g; 1.05 equiv; 18.21 mmoles) and diisopropylethylamine (9.08 mL; 3.0 equiv; 52.04 mmoles) and maintain the reaction at 40° C. for 4 hours. Load the solution directly onto a diisopropylethylamine treated silica gel column and purify the mixture by column chromatography (0 to 15% methanol in ethyl acetate) to give 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate (3.32 g; 44%) as a colorless foam. MS (m/z): 431(M+1).

Examples 2 and 3

Purification of racemic 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate into isomer 1 and 2

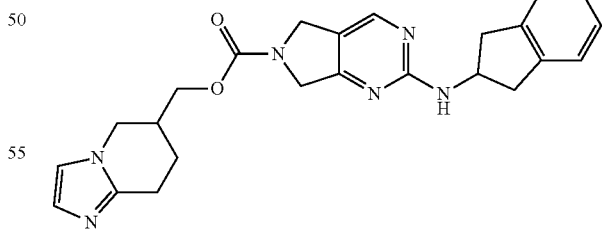

Purify racemic 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate (3.32 g; 1.00 equiv; 7.71 mmoles) by chiral separation. Solubilize the above sample in methanol (63.5 mL), and separate via 10 mL injections onto a Chiralpak AS (20 um) 8×35 cm column at 400 mL/min with 100% methanol (0.2% isopropyl amine), 235 nM wavelength.

Example 2: Isolation of first eluting peak (1) at 8.0 min affords 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate isomer 1 as a tan foam, 99% ee, (1.18 g; 36%), MS (m/z): 431(M+1).

Example 3: Isolation of second eluting peak (2) at 12.0 min, affords 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate isomer 2 as a tan foam, 99% ee, (1.03 g; 31%), MS (m/z): 431(M+1).

Example 4

Synthesis of 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate hydrochloride isomer 1

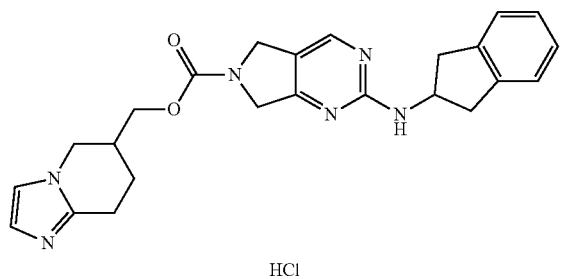 [SMILES: O=C(OCC1CCc2nccn2C1)N1Cc2cnc(NC3Cc4ccccc4C3)nc2C1 ; Cl]

HCl

Add hydrogen chloride (1N, 0.53 mL; 1.0 equiv; 0.53 mmoles) to a solution of 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate isomer 1 (0.228 g; 1.0 equiv; 0.53 mmoles) in methanol (0.5 mL). Swirl the mixture until dissolution occurs and then concentrate to a residue. Add water (1 mL), freeze the solution in a −78° C. dry ice bath, and lyophilize to afford 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate hydrochloride isomer 1 (0.238 g; 100%) as a tan powder. MS (m/z): 431(M+1).

Example 5

Synthesis of 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate hydrochloride isomer 2

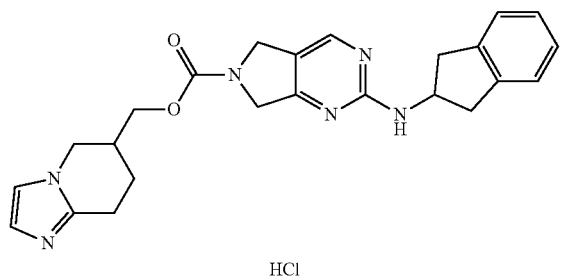 [SMILES: O=C(OCC1CCc2nccn2C1)N1Cc2cnc(NC3Cc4ccccc4C3)nc2C1 ; Cl]

HCl

Add hydrogen chloride (1N, 0.62 mL; 1.05 equiv; 0.62 mmoles) to a solution of 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate isomer 2 (0.254 g; 1.00 equiv; 0.59 mmoles) in isopropyl alcohol (0.3 mL). Swirl the mixture until dissolution occurs, freeze the solution in a −78° C. dry ice bath, and lyophilize to afford 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate hydrochloride isomer 2 (0.28 g; 100%) as a brown foam. MS (m/z): 431(M+1).

Preparation 8

Synthesis of 1-[tert-butyl(diphenyl)silyl]oxy-3-imidazol-1-yl-propan-2-ol

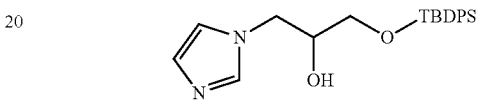

Add 1H-imidazole (19.72 g; 6.2 equiv; 289.67 mmoles) followed by tert-butylchlorodiphenylsilane (12.00 mL; 1.0 equiv; 46.28 mmoles) to a solution of freshly distilled glycidol (5.0 mL; 1.62 equiv; 75.05 mmoles) in acetonitrile (50 mL). Stir the solution at ambient temperature for 30 minutes, then heat to reflux for 4 hours. Allow the mixture to cool to ambient temperature and concentrate the reaction mixture, then pour the residue into dichloromethane/2M sodium bicarbonate (1:1, 400 mL). Separate the layers and further extract the aqueous layer with dichloromethane (2×). Dry the combined organic extracts over magnesium sulfate, filter, and concentrate to afford crude product. Purification by column chromatography affords the desired 1-[tert-butyl(diphenyl)silyl]oxy-3-imidazol-1-yl-propan-2-ol (8.87 g; 50%). MS (m/z): 381(M+1).

Preparation 9

Synthesis of 6-[[tert-butyl(diphenyl)silyl]oxymethyl]-5,6-dihydroimidazo[2,1-c][1,4]oxazin-8-one

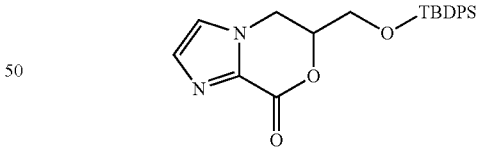

Slowly add trichloromethyl chloroformate (8.74 mL; 2.0 equiv; 72.84 mmoles) over 10 minutes to a 0° C. solution of 1-[tert-butyl(diphenyl)silyl]oxy-3-imidazol-1-yl-propan-2-ol (13.86 g; 1.0 equiv; 36.42 mmoles) and pyridine (23.56 mL; 8 equiv; 291.36 mmoles) in acetonitrile (500 mL). Stir for 1 hour and then allow the solution to warm to ambient temperature over 1 hour. Add water (50 mL) and concentrate the reaction mixture to 75 mL volume. Add dichloromethane (100 mL), and slowly pour the resulting solution into 50% saturated sodium bicarbonate (200 mL). Separate the layers and further extract the aqueous layer with dichloromethane (3×150 mL). Dry the combined organic extracts over magnesium sulfate, filter, and concentrate. Purification by column chromatography (10% to 100% ethyl acetate in hexanes) affords the desired 6-[[tert-butyl(diphenyl)silyl]oxymethyl]-5,6-dihydroimidazo[2,1-c][1,4]oxazin-8-one (9.48 g; 64%) as a light pink gum: MS (m/z): 407(M+1).

Preparation 10

Synthesis of 1-[tert-butyl(diphenyl)silyl]oxy-3-[2-(hydroxymethyl)imidazol-1-yl]propan-2-ol

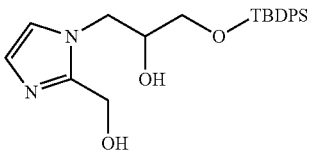

Add diisobutylaluminum hydride (35 mL; 1M in hexanes; 1.5 equiv; 35 mmoles) to a 0° C. solution of 6-[[tert-butyl(diphenyl)silyl]oxymethyl]-5,6-dihydroimidazo[2,1-c][1,4]oxazin-8-one (9.48 g; 1.0 equiv; 23.32 mmoles) in dichloromethane (200 mL). Stir the solution for 15 minutes, then add methanol (150 mL). After 5 minutes, add sodium borohydride (0.176 g; 0.2 equiv; 4.66 mmoles) and maintain the solution at 0° C. for 15 minutes. Add saturate sodium potassium tartrate (50 mL) and stir the solution at ambient temperature for 20 minutes. Concentrate the solution to ~100 mL, add water and dichloromethane (100 mL each), and separate the layers. Further extract the aqueous layer with dichloromethane (5×). Dry the combined organic extracts over magnesium sulfate, filter, and concentrate to afford the desired 1-[tert-butyl(diphenyl)silyl]oxy-3-[2-(hydroxymethyl)imidazol-1-yl]propan-2-ol (9.40 g; 98%). MS (m/z): 411 (M+1).

Preparation 11

Synthesis of tert-butyl-(6,8-dihydro-5H-imidazo[2,1-c][1,4]oxazin-6-ylmethoxy)-diphenyl-silane

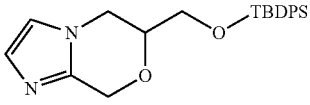

Add iodine (6.39 g; 1.1 equiv; 25.18 mmoles) to a 0° C. solution of triphenylphosphine (7.21 g; 1.2 equiv; 27.47 mmoles) in dichloromethane (60 mL) and stir for 10 minutes. Add 1-methylimidazole (2.19 mL; 1.2 equiv; 27.47 mmoles), resulting in an orange solution with some precipitation.

Separately, prepare a −78° C. solution of 1-[tert-butyl(diphenyl)silyl]oxy-3-[2-(hydroxymethyl)imidazol-1-yl] propan-2-ol (9.4 g; 1.0 equiv; 22.89 mmoles) in dichloromethane (100 mL). Add the in situ prepared iodinating reagent dropwise to this solution with the orange color quickly fading to nearly colorless. Maintain the solution at −78° C. for 30 minutes, then allow it to warm to 0° C. and maintain for 10 minutes. Recool the solution to −78° C., and add tetrahydrofuran (150 mL) followed by 60% sodium hydride (2.20 g; 2.4 equiv; 54.95 mmoles). Slowly warm the solution to 0° C. over 30 minutes, and then to ambient temperature for 1 hour. Pour the mixture slowly into 50% saturated sodium bicarbonate solution and extract with dichloromethane (4×100 mL). Dry the combined organic extracts over magnesium sulfate, filter, and concentrate. Purify the crude product by column chromatography (10 to 100% ethyl acetate in hexanes) to afford the desired product contaminated with triphenylphosphine oxide. Further purify by SCX ion-exchange chromatography (10% methanol in dichloromethane to 10% (4N ammonia in methanol) in dichloromethane) to afford the desired tert-butyl-(6,8-dihydro-5H-imidazo[2,1-c][1,4]oxazin-6-ylmethoxy)-diphenyl-silane (5.96 g; 66%) as a colorless gum. MS (m/z): 393(M+1).

Preparation 12

Synthesis of 6,8-dihydro-5H-imidazo[2,1-c][1,4]oxazin-6-ylmethanol

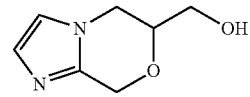 [SMILES: OCC1Cn2ccnc2CO1]

Add tetra-N-butylammonium fluoride (1M in tetrahydrofuran; 13.98 mL; 3 equiv; 13.98 mmoles) to a solution of tert-butyl-(6,8-dihydro-5H-imidazo[2,1-c][1,4]oxazin-6-ylmethoxy)-diphenyl-silane (6.96 g; 1.0 equiv; 17.73 mmoles) in tetrahydrofuran (100 mL) and stir for 1 hour. Load the solution directly onto an SCX ion-exchange column and elute with 15% methanol in dichloromethane followed by 20% ((2N ammonia in methanol) in dichloromethane) to afford (2 scx ion-exchange purifications were required) 6,8-dihydro-5H-imidazo[2,1-c][1,4]oxazin-6-ylmethanol (2.59 g; 61%). MS (m/z): 155(M+1).

Example 6

Synthesis of 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate

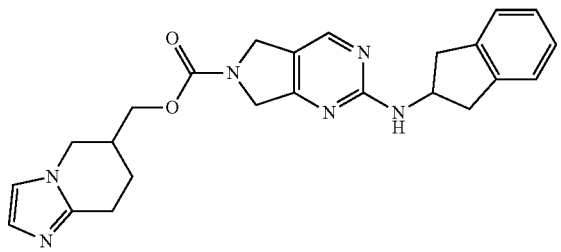 [SMILES: O=C(OCC1CCc2nccn2C1)N1Cc2cnc(NC3Cc4ccccc4C3)nc2C1]

Add 1,1'-carbonyldiimidazole (1.92 g; 1.1 equiv; 11.83 mmoles) to a solution of 6,8-dihydro-5H-imidazo[2,1-c][1,4]oxazin-6-ylmethanol (2.59 g; 1.0 equiv; 10.75 mmoles) in dichloromethane (30 mL) and heat to 40° C. for 1 hour. Add N-(2,3-dihydro-1H-inden-2-yl)-6,7-dihydro-5H-pyrrolo[3,4-d]pyrimidin-2-amine dihydrochloride hydrate (4.80 g; 1.3 equiv; 13.98 mmoles) and triethylamine (4.50 mL; 3 equiv; 32.26 mmoles) and maintain the reaction at 40° C. for 1 hour. Load the solution directly onto a silica gel column and purify by column chromatography (hexanes to ethyl acetate to 20% methanol in ethyl acetate) to give product with significant imidazole present by NMR. Dissolve the crude product in dichloromethane (20 mL) and water (20 mL), separate the layers, and extract with dichloromethane (3×15 mL). Dry the combined organic extracts over magnesium sulfate, filter, and concentrate to give 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate (3.95 g; 85%) as a tan foam. MS (m/z): 433(M+1).

Examples 7 and 8

Purification of racemic 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate into isomer 1 and 2

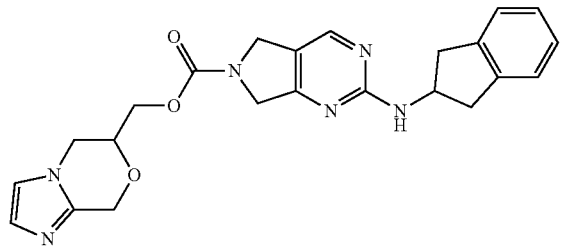 [SMILES: O=C(OCC1Cn2ccnc2CO1)N1Cc2cnc(NC3Cc4ccccc4C3)nc2C1]

Dissolve 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate (3.95 g) in 75.5 mL methanol. Separate via 10 mL injections onto a Chiralpak™ AS (20 um) 50×150 mm column at 400 mL/min with 100% methanol (0.2% isopropylamine), 235 nM wavelength.

Example 7: Isolation of first eluting peak (1) at 8 8 min affords 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate isomer 1 as a tan foam, 99% ee, (1.56 g; 33%). MS (m/z): 433(M+1).

Example 8: Isolation of second eluting peak (2) at 12.8 min affords 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate isomer 2 as a tan foam, 99% ee, (1.60 g; 34%). MS (m/z): 433(M+1).

Example 9

Synthesis of 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate hydrochloride isomer 1

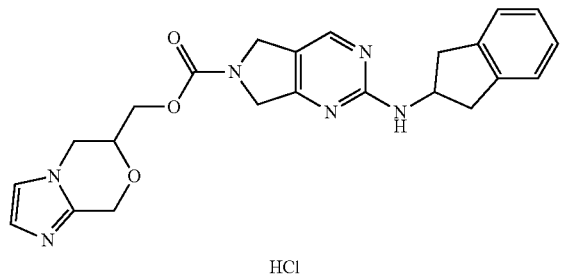 [SMILES: O=C(OCC1Cn2ccnc2CO1)N1Cc2cnc(NC3Cc4ccccc4C3)nc2C1 ; Cl]

Add hydrochloric acid (1N, 3.61 mL; 3.61 mmoles) to a vial containing 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate isomer 1 (1.56 g, 3.61 mmoles) in methanol (1 mL). Freeze this solution in a −78° C. dry ice bath and lyophilize to give 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate hydrochloride isomer 1 (1.67 g). MS (m/z): 433(M+1).

Example 10

Synthesis of 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate hydrochloride isomers 2

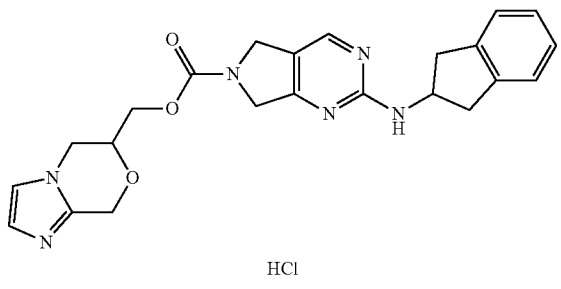 [SMILES: O=C(OCC1Cn2ccnc2CO1)N1Cc2cnc(NC3Cc4ccccc4C3)nc2C1 ; Cl]

Add hydrochloric acid (1N, 3.7 mL; 3.70 mmol) to a vial containing 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate isomer 2 (1.60 g, 3.70 mmoles) in methanol (1 mL). Freeze this solution in a −78° C. dry ice bath and lyophilize to give 5,6-dihydro-8H-imidazo[2,1-c][1,4]oxazin-6-ylmethyl 2-(2,3-dihydro-1H-inden-2-ylamino)-5,7-dihydro-6H-pyrrolo[3,4-d]pyrimidine-6-carboxylate hydrochloride isomer 2 (1.65 g). MS (m/z): 433(M+1).

Preparation 13

Synthesis of (2R)-1-[tert-butyl(diphenyl)silyl]oxy-3-imidazol-1-yl-propan-2-ol

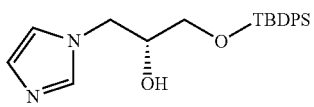

Add 1H-imidazole (14.70 g; 4 equiv; 215.99 mmoles) followed by tert-butylchlorodiphenylsilane (14.00 mL; 1.0 equiv; 54.00 mmoles) to a 0° C. solution of freshly distilled (S)-glycidol (3.66 mL; 1.0 equiv; 54.00 mmoles) in acetonitrile (40 mL). Stir the solution at ambient temperature for 30 minutes, then heat to reflux for 4 hours. Allow the mixture to cool to ambient temperature and concentrate the reaction mixture, then pour the residue into dichloromethane and 2M sodium bicarbonate solution (1:1, 400 mL). Separate the layers and further extract the aqueous layer with dichloromethane (2×). Dry the combined organic extracts over magnesium sulfate, filter, and concentrate to afford crude product. Purification by column chromatography affords the desired (2R)-1-[tert-butyl(diphenyl)silyl]oxy-3-imidazol-1-yl-propan-2-ol (9.25 g; 45%). MS (m/z): 381(M+1).

Preparation 14

Synthesis of (6R)-6-[[tert-butyl(diphenyl)silyl]oxymethyl]-5,6-dihydroimidazo[2,1-c][1,4]oxazin-8-one

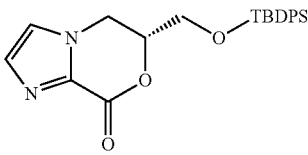

Slowly add trichloromethyl chloroformate (5.80 mL; 2.0 equiv; 48.35 mmoles) over 15 minutes to a 0° C. solution of (2R)-1-[tert-butyl(diphenyl)silyl]oxy-3-imidazol-1-yl-propan-2-ol (9.2 g; 1.0 equiv; 24.17 mmoles) and pyridine (15.64 mL; 8 equiv; 193.40 mmoles) in acetonitrile (450 mL). Stir for 1 hour and then allow the solution to warm to ambient temperature over 1 hour. Add water (30 mL) and concentrate the reaction mixture. Add dichloromethane (50 mL), and slowly pour the resulting solution into 50% saturated sodium bicarbonate (200 mL). Separate the layers and further extract the aqueous layer with dichloromethane (3×150 mL). Dry the combined organic extracts over magnesium sulfate, filter, and concentrate. Purification by column chromatography (10% to 100% ethyl acetate in hexanes) affords the desired (6R)-6-[[tert-butyl(diphenyl)silyl]oxymethyl]-5,6-dihydroimidazo[2,1-c][1,4]oxazin-8-one (5.50 g; 56%). MS (m/z): 407(M+1).

Preparation 15

Synthesis of (2R)-1-[tert-butyl(diphenyl)silyl]oxy-3-[2-(hydroxymethyl)imidazol-1-yl]propan-2-ol

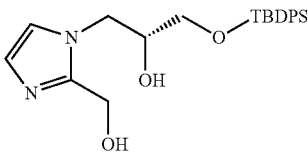

Add diisobutylaluminum hydride (1M in hexanes; 21.65 mL; 1.6 equiv; 21.65 mmoles) to a 0° C. solution of (6R)-6-[[tert-butyl(diphenyl)silyl]oxymethyl]-5,6-dihydroimidazo[2,1-c][1,4]oxazin-8-one (5.5 g; 1.0 equiv; 13.53 mmoles) in dichloromethane (130 mL). Stir the solution for 15 minutes, then add methanol (100 mL). After 5 minutes, add sodium borohydride (0.307 g; 0.6 equiv; 8.12 mmoles) and maintain the solution at 0° C. for 15 minutes. Add saturated sodium potassium tartrate solution (80 mL) and stir the solution at ambient temperature for 14 hours. Filter the solution and separate the liquid layers. Further extract the aqueous layer with dichloromethane (3×). Wash the combined organic extracts with 50% saturated brine, dry over magnesium sulfate, filter, and concentrate to afford the desired (2R)-1-[tert-butyl(diphenyl)silyl]oxy-3-[2-(hydroxymethyl)imidazol-1-yl]propan-2-ol (5.30 g; 95%). MS (m/z): 411 (M+1).

Preparation 16

Synthesis of tert-butyl-[[(6R)-6,8-dihydro-5H-imidazo[2,1-c][1,4]oxazin-6-yl]methoxy]-diphenyl-silane

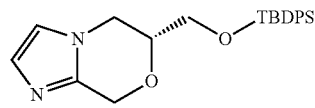

Add iodine (3.44 g; 1.05 equiv; 13.55 mmoles) to a 0° C. solution of triphenylphosphine (4.06 g; 1.2 equiv; 15.49 mmoles) in dichloromethane (25 mL) and stir for 10 minutes. Add 1-methylimidazole (1.23 mL; 1.2 equiv; 15.49 mmoles), resulting in an orange solution with some precipitation.
Separately, prepare a −78° C. solution of (2R)-1-[tert-butyl(diphenyl)silyl]oxy-3-[2-(hydroxymethyl)imidazol-1-yl]propan-2-ol (5.3 g; 1.0 equiv; 12.91 mmoles) in dichloromethane (25 mL). Add the in situ prepared iodinating reagent dropwise to the solution of (2R)-1-[tert-butyl(diphenyl)silyl]oxy-3-[2-(hydroxymethyl)imidazol-1-yl]propan-2-ol, with the orange color quickly fading to nearly colorless. Maintain the solution at −78° C. for 30 minutes, then allow it to warm to 0° C. and maintain for 10 minutes. Re-cool the solution to −78° C., and add tetrahydrofuran (100 mL) followed by 60% sodium hydride (1.14 g; 2.2 equiv; 28.40 mmoles). Slowly warm the solution to 0° C. over 30 minutes, and then to ambient temperature for 1 hour. Pour the mixture slowly into 50% saturated sodium bicarbonate solution and extract with dichloromethane (4×100 mL). Dry the combined organic extracts over magnesium sulfate, filter, and concentrate. Purify the crude product by column chromatography (10 to 100% ethyl acetate in hexanes) to afford the desired product contaminated with triphenylphosphine oxide. Further purify by SCX ion-exchange chromatography (10% methanol in dichloromethane to 10% (4N ammonia in methanol) in dichloromethane) to afford the desired tert-butyl-[[(6R)-6,8-dihydro-5H-imidazo[2,1-c][1,4]oxazin-6-yl]methoxy]-diphenyl-silane (1.86 g; 37%). MS (m/z): 393(M+1).

Preparation 17

Synthesis of [(6R)-6,8-dihydro-5H-imidazo[2,1-c][1,4]oxazin-6-yl]methanol

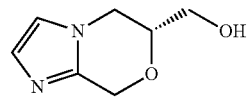

Add cesium fluoride (1.42 g; 2.0 equiv; 9.32 mmoles) to a solution of [(6R)-6,8-dihydro-5H-imidazo[2,1-c][1,4]oxazin-6-yl]methanol (1.83 g; 1.0 equiv; 4.66 mmoles) in tetrahydrofuran (25 mL), water (5 mL), and dimethylformamide (5 mL) and stir for 36 hours. No reaction occurs, so add tetra-N-butylammonium fluoride (1 N in tetrahydrofuran; 13.98 mL; 3 equiv; 13.98 mmoles) and stir for 1 hour. Load the solution directly onto an SCX ion-exchange column and elute with 15% methanol in dichloromethane followed by 20% (2N ammonia in methanol) in dichloromethane to afford the desired product contaminated with what is likely alkylammonium salts. Further purify the crude product by column chromatography(1 to 10% methanol/chloroform) to afford the desired [(6R)-6,8-dihydro-5H-imidazo[2,1-c][1,4]oxazin-6-yl]methanol (0.515 g; 72%). MS (m/z): 155(M+1).

Example 11

Synthesis of [(6R)-6,8-dihydro-5H-imidazo[2,1-c][1,4]oxazin-6-yl]methyl 2-(indan-2-ylamino)-5,7-dihydropyrrolo[3,4-d]pyrimidine-6-carboxylate

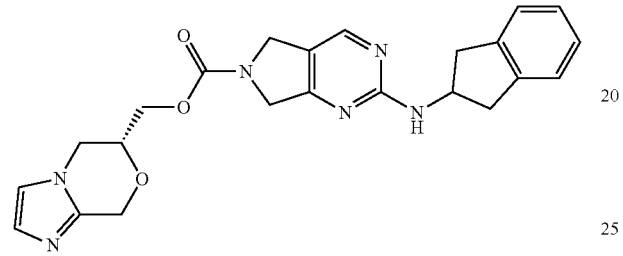

Add 1,1'-carbonyldiimidazole (0.477 g; 1.1 equiv; 2.94 mmoles) to a solution of [(6R)-6,8-dihydro-5H-imidazo[2,1-c][1,4]oxazin-6-yl]methanol (0.412 g; 1.0 equiv; 2.67 mmoles) in 1,2-dichloroethane (15 mL) and tetrahydrofuran (5 mL). Heat the solution to 50° C. for 30 minutes, then add N-(2,3-dihydro-1h-inden-2-yl)-6,7-dihydro-5H-pyrrolo[3,4-d]pyrimidin-2-amine dihydrochloride hydrate (1.01 g; 1.1 equiv; 2.94 mmoles) followed by triethylamine (1.30 mL; 3.5 equiv; 9.35 mmoles). Stir the resulting solution for 3 hours at 50° C. Pour the mixture into 50% saturated sodium bicarbonate and dichloromethane (50 mL each). Separate the layers and further extract the aqueous layer with dichloromethane (2×50 mL). Dry the combined organic extracts over magnesium sulfate, filter, and concentrate to give a red oil. Purify the crude product by column chromatography (1 to 8% methanol in chloroform) to afford the desired [(6R)-6,8-dihydro-5H-imidazo[2,1-c][1,4]oxazin-6-yl]methyl 2-(indan-2-ylamino)-5,7-dihydropyrrolo[3,4-d]pyrimidine-6-carboxylate (1.12 g; 97%). Determine enantiomeric excess by chiral HPLC analysis (0.46×15 cm Chiralpak™ AS-H column, 100% methanol elution). Isolated product elutes at 13 minutes whereas the enantiomer elutes at 9.1 minutes, demonstrating the product to be 98.3% ee. MS (m/z): 433(M+1).

Preparation 18

Synthesis of 6-methoxy-5,6,7,8-tetrahydroimidazo[1,2-a]pyridine

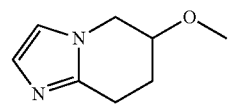

Add acetic acid (40 mL) to a heterogeneous solution of 6-methoxyimidazopyridine (1.0 g; 1.0 equiv; 6.75 mmoles) and 10% palladium on carbon (1.0 g; 1.4 equiv; 9.40 mmoles). Evacuate and backfill the reaction vessel with nitrogen (3×) then hydrogen (3×). Vigorously stir the reaction under hydrogen at ambient temperature for 3 hours. Filter the reaction mixture through celite, and wash the filter cake with a 1:1 mixture of dichloromethane and methanol. Concentrate the filtrate and dissolve the crude product mixture in 20 mL methanol, then load onto a scx ion-exchange column. Elute with methanol followed by 2M ammonia in methanol to give 6-methoxy-5,6,7,8-tetrahydroimidazo[1,2-a]pyridine (1.00 g; 97%) as a colorless oil. ¹H NMR (DMSO): δ 1.84-1.94 (m, 1H), 2.00-2.09 (m, 1H), 2.63-2.68 (m, 2H), 3.27 (s, 3H), 3.77-3.82 (m, 1H), 3.92-4.03 (m, 2 H), 6.74 (d, 1H), 6.91 (d, 1H).

Preparation 19

Synthesis of 5,6,7,8-tetrahydroimidazo[1,2-a]pyridin-6-ol

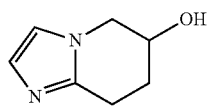

Add boron tribromide (1.24 mL; 2.0 equiv; 13.14 mmoles) to a solution of 6-methoxy-5,6,7,8-tetrahydroimidazo[1,2-a]pyridine (1.0 g; 1.0 equiv; 6.57 mmoles) in dichloromethane (40 mL) dropwise and stir at ambient temperature for 4 hours. Add water (10 mL) and stir for 20 minutes, then concentrate the mixture. Add methanol (20 mL) and load the solution onto an scx ion-exchange column. Purify the product by eluting with methanol followed by 2M ammonia in methanol to give 5,6,7,8-tetrahydroimidazo[1,2-a]pyridin-6-ol (0.908 g; 80% yield), which crystallizes upon standing. MS (m/z): 139 (M+1).

Preparation 20

Synthesis of tert-butyl 2-(5,6,7,8-tetrahydroimidazo[1,2-a]pyridin-6-yloxy)acetate

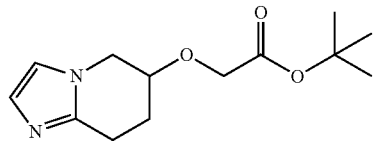 [SMILES: CC(C)(C)OC(=O)COC1CCc2nccn2C1]

Warm a suspension of 5,6,7,8-tetrahydroimidazo[1,2-a]pyridin-6-ol (0.357 g; 1.0 equiv; 2.07 mmoles) in dimethylformamide (4 mL) to 40° C. get full dissolution, then cool to 0° C. and add sodium hydride (0.091 g 1.1 equiv; 2.27 mmoles) and stir for 30 minutes. Add acetic acid, bromo-1,1-dimethylethyl ester (1.1 equiv; 1.10 equiv; 2.27 mmoles; 342.48 μL) dropwise at 0° C. and stir for 1 hour. Dilute the reaction mixture with methanol (10 mL) and pass through a scx ion-exchange column (methanol to 2M ammonia in methanol) to provide tert-butyl 2-(5,6,7,8-tetrahydroimidazo[1,2-a]pyridin-6-yloxylacetate (0.3 g; 17%) as a yellow gum, which is used directly in next step. MS (m/z): 253(M+1).

Example 12

Preparation of 1-[2-(2,3-dihydro-1H-inden-2-ylamino)-5,7-dihydro-6H-pyrrolo[3,4-d]pyrimidin-6-yl]-2-(5,6,7,8-tetrahydroimidazo[1,2-a]pyridin-6-yloxy)ethanone

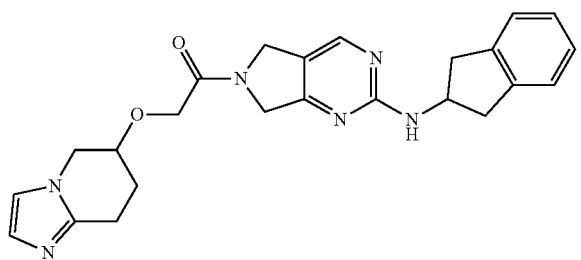 [SMILES: O=C(COC1CCc2nccn2C1)N1Cc2cnc(NC3Cc4ccccc4C3)nc2C1]

Add trifluoroacetic acid (3 mL) to a flask containing tert-butyl 2-(5,6,7,8-tetrahydroimidazo[1,2-a]pyridin-6-yloxy)acetate (0.30 g; 2.04 equiv; 1.19 mmoles) in dichloromethane (3 mL), and stir at ambient temperature for 1 hour. Concentrate the mixture, add toluene (2×5 mL), and reconcentrate (2×). Add methanol (10 mL) followed by 5 N hydrochloric acid (1 mL), then concentrate. Add toluene (4×5 mL) and reconcentrate (4×). Add dimethylformamide (5 mL), triethylamine (15 equiv; 8.74 mmol; 1.22 mL), N-(2,3-dihydro-1H-inden-2-yl)-6,7-dihydro-5H-pyrrolo[3,4-d]pyrimidin-2-amine dihydrochloride hydrate (0.20 g; 1.0 equiv; 0.583 mmoles) and 1-propanephosphonic acid cyclic anhydride (0.70 mL; 2.0 equiv; 1.17 mmoles) and stir at ambient temperature for 2 hours. Load the solution directly onto a silica gel column and purify by column chromatography (hexanes to ethyl acetate to 20% methanol in ethyl acetate) to give impure product. Further purify the crude product by reverse phase chromatography to afford 1-[2-(2,3-dihydro-1H-inden-2-ylamino)-5,7-dihydro-6H-pyrrolo[3,4-d]pyrimidin-6-yl]-2-(5,6,7,8-tetrahydroimidazo[1,2-a]pyridin-6-yloxy) ethanone (0.083 g; 33%) as a light yellow foam. MS (m/z): 431(M+1).

Examples 13 and 14

Purification of 1-[2-(2,3-dihydro-1H-inden-2-ylamino)-5,7-dihydro-6H-pyrrolo[3,4-d]pyrimidin-6-yl]-2-(5,6,7,8-tetrahydroimidazo[1,2-a]pyridin-6-yloxy)ethanone into isomer 1 and 2

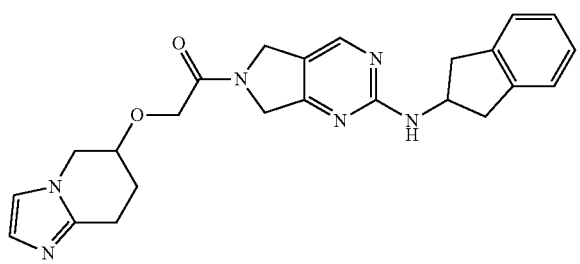 [SMILES: O=C(COC1CCc2nccn2C1)N1Cc2cnc(NC3Cc4ccccc4C3)nc2C1]

Suspend 1-[2-(2,3-dihydro-1H-inden-2-ylamino)-5,7-dihydro-6H-pyrrolo[3,4-d]pyrimidin-6-yl]-2-(5,6,7,8-tetrahydroimidazo[1,2-a]pyridin-6-yloxy)ethanone (0.083 g; 1.0 equiv; 0.193 mmoles) in 1.0 mL methanol and add several drops of isopropyl alcohol to solubilize it. Inject series of 0.5 mL into a column (2.1×25 cm Chiralcel™ OD-H, 5 micron, eluting a with mobile phase of 40% methanol (0.2% isopropylamine)/carbon dioxide. (Flow 70 mL/min 225 nm detection).

Example 13: Isolation of first eluting peak (1) at 8.0 min affords 1-[2-(2,3-dihydro-1H-inden-2-ylamino)-5,7-dihydro-6H-pyrrolo[3,4-d]pyrimidin-6-yl]-2-(5,6,7,8-tetrahydroimidazo[1,2-a]pyridin-6-yloxy)ethanone isomer 1 as a colorless foam, 99% ee, (0.030 g; 36%). MS (m/z): 431(M+1).

Example 14: Isolation of second eluting peak (2) at 11.8 min affords –[2-(2,3-dihydro-1H-inden-2-ylamino)-5,7-dihydro-6H-pyrrolo[3,4-d]pyrimidin-6-yl]-2-(5,6,7,8-tetrahydroimidazo[1,2-a]pyridin-6-yloxy)ethanone isomer 2 as a colorless foam, 99% ee, (0.042 g; 51%). MS (m/z): 431(M+1).

Preparation 21

Synthesis of 2-chloro-1-[2-(2,3-dihydro-1H-inden-2-ylamino)-7,8-dihydropyrido[4,3-d]pyrimidin-6(5H)-yl]ethanone

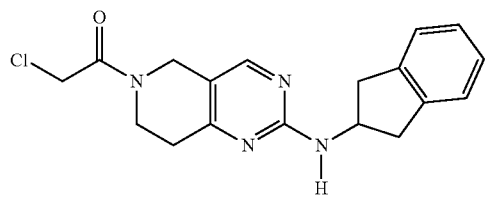 [SMILES: O=C(CCl)N1CCc2nc(NC3Cc4ccccc4C3)ncc2C1]

To N-indan-2-yl-5,6,7,8-tetrahydropyrido[4,3-d]pyrimidin-2-amine (11.0 g, 41.3 mmol) and triethylamine (7.48 mL, 53 7 mmol) in dichloromethane (200 mL), add 2-chloroacetyl chloride (3.61 mL, 5.13 g, 45.4 mmol) dropwise over five minutes at 23° C. Stir for 30 minutes and pour the reaction mixture into 1:1 50% saturated aqueous sodium bicarbonate:dichloromethane (75 mL). Separate the organic layer from the aqueous layer and further extract the aqueous layer with dichloromethane (2×25 mL). Combine the organic extracts and dry over anhydrous sodium sulfate, filter, and concentrate. Dissolve the residue in chloroform (10 mL) and purify via silica gel column chromatography (gradient elution: 25% ethyl acetate in hexanes to 100% ethyl acetate) to give the title compound (9.75 g, 69%). $^1$H NMR (CDCl$_3$, *=minor amide rotamer) δ 2.77* (t, 2H), 2.84 (dd, 2H), 2.87 (t, 2H), 3.35 (dd, 2H), 3.76 (t, 2H), 3.85* (t, 2H), 4.12 (s, 2H), 4.52* (s, 2H), 4.57 (s, 2H), 4.72-4.82 (m, 1H), 5.48-5.64 (m, 1H), 7.12-7.21 (m, 4H), 8.03-8.10 (m, 1H).

Example 15

Synthesis of 1-[2-(2,3-dihydro-1H-inden-2-ylamino)-7,8-dihydropyrido[4,3-d]pyrimidin-6(5H)-yl]-2-(5,6,7,8-tetrahydroimidazo[1,2-a]pyridin-6-yloxy)ethanone

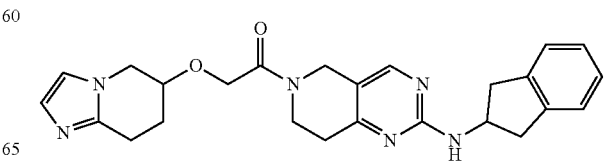

Add sodium hydride (0.054 g; 1.85 equiv; 1.35 mmoles) to a solution of 5,6,7,8-tetrahydroimidazo[1,2-a]pyridin-6-ol (0.252 g; 2.0 equiv; 1.46 mmoles) in dimethylformamide (2 mL) and stir at room temperature for 10 minutes. Add this mixture to a 0° C. solution of 2-chloro-1-[2-(2,3-dihydro-1H-inden-2-ylamino)-7,8-dihydropyrido[4,3-d]pyrimidin-6(5H)-yl]ethanone (0.25 g; 1.0 equiv; 0.729 mmoles) in dimethylformamide (2 mL). Stir the resulting solution at 0° C. for 1 hour, then add water and load onto a SCX ion exchange column. Elute off the crude product (methanol to 7N ammonia in methanol). Further purify the product by reverse phase chromatography to afford 1-[2-(2,3-dihydro-1H-inden-2-ylamino)-7,8-dihydropyrido[4,3-d]pyrimidin-6(5H)-yl]-2-(5,6,7,8-tetrahydroimidazo[1,2-a]pyridin-6-yloxy)ethanone (0.035 g; 11%) as a white foam. MS (m/z): 445(M+1).

Inhibition of Autotaxin as Measured by Choline Release

The purpose of this assay is to detect autotaxin inhibition using a choline release assay.

Test compounds (10 mM stocks in 100% DMSO) are serially diluted in 100% DMSO resulting in 10 concentrations of 100× inhibitor in half area 96 well plates (Corning 3992). Each of these 10 wells in 100% DMSO is diluted 1:33.33 in assay buffer in round bottom 96 well plates (Fisher 12565502) resulting in 3× concentrations in well containing 3% DMSO. The assay buffer is 50 mM Tris pH8.0, 5 mM KCl, 1 mM $CaCl_2$, 1 mM $MgCl_2$, 0.01% TRITON™ X-100 (Sigma T9284) and 0.01% fatty acid free bovine serum albumin (Sigma A8806). A 20 µl aliquot of each 3× test compound is then added to black flat bottom 96 well plates (Corning 3991) in singlicate. A 20 µl aliquot per well of 3× recombinant human autotaxin (full length human autotaxin with a C-terminal His tag transfected into 293E cells and purified via nickel chelate and size exclusion chromatography) is then added to every well except for the no enzyme control wells. A 20 µl aliquot per well of assay buffer is added to the no enzyme control wells. A 20 µl aliquot of a 3× cocktail containing choline oxidase (Sigma C5896), horseradish peroxidase (Sigma P8125), amplex ultrared (Invitrogen A36006) and the autotaxin substrate lysophosphatidylcholine (LPC) 16:0 (Avanti Polar Lipids 855675P) is added to each well while avoiding exposure to light. The final concentrations in the well of choline oxidase, horseradish peroxidase, amplex ultrared and LPC 16:0 are 0.4 units/ml, 4 units/ml, 40 µM and 30 µM respectively. The plate is then sealed with aluminum foil seals and incubated at 37° C. for 1 hour in a Labline Imperial III incubator. During this incubation, LPC is cleaved by autotaxin resulting in Lysophosphatidic Acid (LPA) 16:0 and choline. The choline that is released is oxidized by choline oxidase resulting in betaine and hydrogen peroxide. The hydrogen peroxide reacts with the horseradish peroxide and amplex ultrared to form the fluorescent molecule resorufin. The resorufin on the plates is measured with a SpectraMax Gemini EM fluorometer at excitation-emission wavelengths of 530-590 nm using SoftMax Pro 4.8 software. $IC_{50}$s are calculated using 4 parameter curve fits with the internal Lilly software OLO curve fitting tool. Results are expressed as the arithmetic mean +/− standard deviation; n=x. The compounds of Examples 1-15 herein were tested essentially as described above, and exhibited an $IC_{50}$ for autotaxin of lower than about 100 nM. The following exemplified compounds were tested essentially as described above and exhibited the following activity for autotaxin:

TABLE 1

| Inhibition of Autotaxin: Choline Release Assay | |
|---|---|
| Test Compound | $IC_{50}$ (nM) |
| Example 3 | <1.70 (n = 5) |
| Example 8 | 2.04 (n = 6) |

The data in Table 1 illustrate that the compounds of Table 1 inhibit autotaxin using the in vitro choline release assay.

Reduction of LPA in the Presence of Human Plasma

The following assay is intended to measure the reduction of LPA. This assay is a tool that can be used to identify selective autotaxin-mediated LPA inhibitor compounds when it is used to test compounds that have been identified as autotaxin inhibitors. LPA biosynthesis through autotaxin is believed to the the source of LPA for $LPA_1$ mediated neuropathic pain. Makoto Inoue, et. al, "*Autotaxin, a synthetic enzyme of lysophosphatidic acid (LPA), mediates the induction of nerve-injured neuropathic pain*", Molecular Pain, 2008, 4:6. Targeted inhibition of the autotaxin mediated LPA biosynthesis is supported by the results of this assay.

Units of plasma from healthy human female donors collected in sodium heparin (Lampire Biologicals) are pooled, aliquoted and stored at −80° C. On the day of assay, aliquots of the plasma are thawed and spun for 10 minutes at 3000 RPMs at 4° C. in a centrifuge to remove debris. A 90 µl aliquot of plasma is added to each well of a 96 well round bottom polypropylene plate. A 10 µL aliquot of 10× test compound containing 10% DMSO in assay buffer (50 mM Tris pH8.0, 5 mM KCl, 1 mM $CaCl_2$, 1 mM $MgCl_2$) is added to each well except for the control wells which contain no test compound. This results in 10 1× concentrations of test compound in singlicate with a final concentration of 1% DMSO in 90% plasma. A 10 µl aliquot of 10% DMSO in assay buffer without test compound is added to the 0 hour (n=8) and 3 hour no test compound controls (n=8) wells. A 10 µl aliquot of 500 mM ethylenediaminetetraacetic acid (EDTA) is added to each of the 0 hour no test compound control wells to chelate endogenous autotaxin. The entire contents of the 0 hour no test compound control wells are transferred to a new 96 well round bottom polypropylene plate and frozen at −80° C. The plate containing plasma +/− test compounds (minus the 0 hour no inhibitor control wells) is then incubated for 3 hours at 37° C. in a Robbins Scientific™ model 400 hybridization incubator while rocking at 14,000 RPMs. During this 3 hour incubation, lecithin cholesterol acyltransferases present in the plasma cleave phosphatidylcholine resulting in higher plasma levels of the autotaxin substrate lysophosphatidylcholine (LPC). The increased endogenous LPC levels are cleaved by endogenous autotaxin resulting in higher plasma concentrations of endogenous lysophosphatidic acid (LPA) (Nakamura et al, Clinical Biochemistry 40 (2007), 274-277). This increase in LPA in the 3 hour incubation can be inhibited by autotaxin inhibitors. Following the 3 hour incubation, 10 µl of 500 mM EDTA is added to all of the remaining wells (test compound containing wells and 3 hour no test compound control wells) to chelate the endogenous autotaxin. The entire contents of these wells are then added to the plate containing the 0 hour no test compound control plasma that had previously been stored at −80° C. (without thawing the 0 hour plasma). The plate is then re-covered with an aluminum foil seal and placed back at −80° C. until extraction for mass spec analysis. On the day of extraction, the plates are thawed on ice and 25 µl of plasma from each well is transferred to a 2 ml TrueTaper™ square 96 deep well plate (Analytical Sales and Products #968820). A 400 μl aliquot of extraction buffer (50% methanol, 49.9% acetonitrile, 0.1% acetic acid) containing LPA internal standards (50 ng/ml D5 deuterium LPA 16:0 and 50 ng/ml D5 deuterium LPA 18:0) is added to each well and the total LPA in each sample is determined by mass spec analysis. Percent reduction of LPA is calculated according to the following formula:

100−(3 hour plasma+test compound−0 hour plasma no test compound control)/(3 hour plasma no test compound control−0 hour plasma no test compound control)×100

$IC_{50}$ values are calculated using 4 parameter curve fitting. Results are expressed as the arithmetic mean +/− standard deviation; n=x. Results of this assay using compounds of this invention show LPA reduction that is dose dependent and statistically significant.

TABLE 2

| Reduction of LPA in Human Plasma | |
|---|---|
| Test Compound | $IC_{50}$ (nM) |
| Example 3 | 2.22 (n = 4) |
| Example 8 | 12.9 (n = 3) |

The data in Table 2 demonstrate that the compounds decrease LPA in the presence of human plasma. The results support that the compounds inhibit autotaxin mediated LPA biosynthesis.

We claim:

1. A compound of the formula I

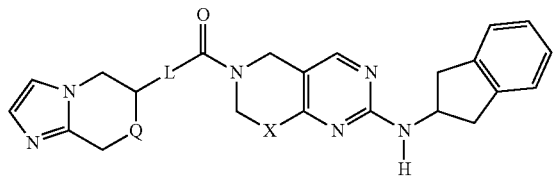

wherein X is a bond;
Q is $CH_2$ or O;
L is selected from the group consisting of —$OCH_2$— and —$CH_2O$—;
or a pharmaceutically acceptable salt thereof.

2. A compound or salt according to claim 1 wherein Q is O.

3. A compound or salt according to claim 1 wherein Q is $CH_2$.

4. A compound or salt according to claim 3 wherein L is —$OCH_2$—.

5. A compound or salt according to claim 1 which is 5,6-dihydro-8H-imidazo [2,1-c][1,4]oxazin-6-ylmethyl 2-(2,3-dihydro-1H-inden-2-ylamino)-5,7-dihydro-6H-pyrrolo[3,4-d]pyrimidine-6-carboxylate:

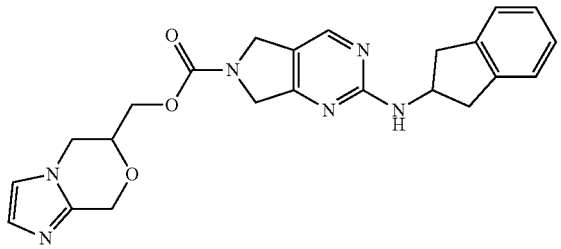

6. A compound or salt according to claim 1 which is 5,6,7,8-tetrahydroimidazo[1,2-a]pyridin-6-ylmethyl 2-(2,3-dihydro-1H-inden-2-ylamino)-5,7-dihydro-6H-pyrrolo[3,4-d]pyrimidine-6-carboxylate:

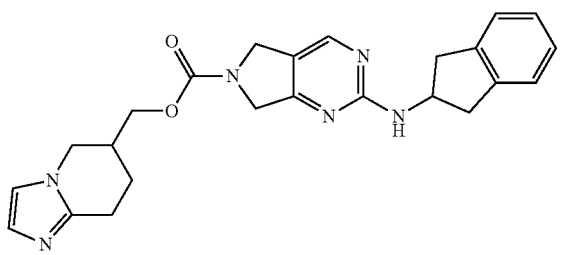

7. A pharmaceutical composition comprising a compound or a pharmaceutically acceptable salt thereof, according to claim 1, in combination with one or more pharmaceutically acceptable carriers, diluents, or excipients.

8. A method of treating pain in a patient, comprising administering to a patient in need thereof, an effective amount of a compound according to claim 1, or a pharmaceutically acceptable salt thereof.

9. A method of treating pain associated with osteoarthritis in a patient, comprising administering to a patient in need thereof, an effective amount of a compound according to claim 1; or a pharmaceutically acceptable salt thereof.

* * * * *